United States Patent [19]

Kanda et al.

[11] Patent Number: 4,905,703
[45] Date of Patent: Mar. 6, 1990

[54] LIVER FUNCTION TESTING APPARATUS AND METHOD

[75] Inventors: Masahiko Kanda; Kunio Awazu, both of Osaka, Japan

[73] Assignee: Sumitomo Electric Industries, Ltd., Osaka, Japan

[21] Appl. No.: 217,877

[22] PCT Filed: Nov. 4, 1987

[86] PCT No.: PCT/JP87/00851
§ 371 Date: Jun. 20, 1988
§ 102(e) Date: Jun. 20, 1988

[87] PCT Pub. No.: WO88/03386
PCT Pub. Date: May 19, 1988

[30] Foreign Application Priority Data

Nov. 5, 1986 [JP] Japan .................... 61-263046
Jul. 13, 1987 [JP] Japan .................... 62-175517

[51] Int. Cl.$^4$ ............................... A61B 5/00
[52] U.S. Cl. ............................... 128/666
[58] Field of Search ............... 128/665–667, 128/633–634

[56] References Cited

U.S. PATENT DOCUMENTS 3,677,648  7/1972  Dorsch .................... 356/40

FOREIGN PATENT DOCUMENTS 57-64044   4/1982  Japan .
59-189828 10/1984  Japan .
61-162934  7/1986  Japan .
61-203939  9/1986  Japan .
61-177608 11/1986  Japan .

Primary Examiner—Francis Jaworski
Attorney, Agent, or Firm—W. G. Fasse; D. H. Kane, Jr.

[57] ABSTRACT

In a liver function testing apparatus, light sources (11, 12) expose vital tissue (15) to a first light of a wavelength absorbed by specific dye dosed into blood of the vital tissue, whereby the dye is to be taken in and removed by a liver and a second light of a wavelength not absorbed by the dye. Optical pulses obtained from the vital tissue are received by a light receiving element (13) providing an output signal which is sampled by an A-D converter (30) for converting the output signal into digital sampling signals. Variable components in the blood represented by the sampling signals are determined as coefficients of linear functions, to perform a biocalibration. A value correlated with a specific dye concentration in the blood is processed on the basis of the digital sampling signals during a prescribed period after injection of a defined dose of the specific dye and on the basis of the determined coefficients, so that a coefficient of a simulation function which is a function of time is obtained by using the method of least squares. Additionally a blood plasma disappearance rate and a retention rate are obtained on the basis of the coefficient.

32 Claims, 18 Drawing Sheets

FIG.1

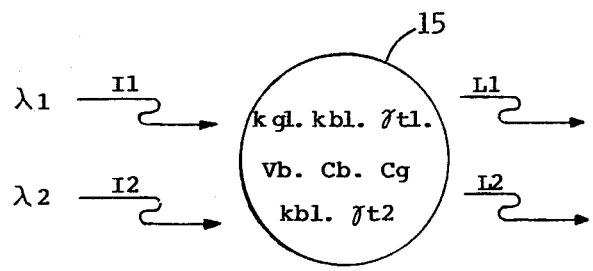

VITAL TISSUE $k_{g1}$ : ABSORPTION COEFFICIENT OF SPECIFIC DYE
(WAVELENGTH: $\lambda_1$)

$k_{b1}$ : ABSORPTION COEFFICIENT OF BLOOD AT WAVELENGTH $\lambda_1$ $k_{b2}$ : ABSORPTION COEFFICIENT OF BLOOD AT WAVELENGTH $\lambda_2$ $\gamma_{t1}$ : ABSORBANCE OF TISSUE AT WAVELENGTH $\lambda_1$ $\gamma_{t2}$ : ABSORBANCE OF TISSUE AT WAVELENGTH $\lambda_2$ $V_b$ : BLOOD VOLUME IN SAMPLE $C_b$ : BLOOD CONCENTRATION IN SAMPLE $C_g$ : SPECIFIC DYE CONCENTRATION IN SAMPLE Y = .869716 X
+ .861895
r = .999438

FIG.20

| | |
|---|---|
| L1 | —8a1 |
| L2 | —8a2 |
| LMAX | —8b1 |
| LMIN | —8b2 |
| m | |
| i1 | —8c1 |
| i2 | —8c2 |
| CL1(1) | —8d1 |
| ⋮ | ⋮ |
| CL1(n) | —8dn |
| ITM | —8i1 |
| TIM1 | —8i2 |
| TIM2 | —8i3 |
| k1 | —8k1 |
| rg1 | —8k2 |
| k2 | —8k3 |
| rg2 | —8k4 |
| k3 | —8k5 |
| rg3 | —8k6 |
| CL2(1) | —8e1 |
| ⋮ | ⋮ |
| CL2(n) | —8en |
| A | —8f1 |
| B | —8f2 |
| r1 | —8f3 |
| CL10 | —8f4 |
| Cg(1) | —8g1 |
| ⋮ | ⋮ |
| Cg(m) | —8gm |
| LO λ1 | —8h1 |
| LO λ2 | —8h2 |
| RMAX | —8ℓ1 |
| rMAX | —8ℓ2 |

LIVER FUNCTION TESTING APPARATUS AND METHOD

TECHNICAL FIELD

The present invention relates to a liver function testing apparatus and to a method for testing the function of a liver. More specifically, it relates to a liver function testing apparatus for automatically performing measurements for testing/diagnosing a liver function by injecting a specific color dye, which is selectively taken in and removed only by the liver, into the blood and measuring a blood plasma disappearance rate and a retention rate thereof.

BACKGROUND INFORMATION

In general, the blood plasma disappearance rate and the retention rate have been measured by a method of blood collection through use of indocyanine green (hereinafter referred to as ICG) serving as a specific dye. According to this method, an intravenous injection of ICG is given to a testee and a blood sample is taken three times after lapses of five, ten and 15 minutes from the injection. The blood serum is separated upon coagulation of a blood clot so that an absorbance at a wavelength of 805 nm is measured through a spectrophotometer to obtain ICG concentration values in the blood serum after the lapses of five, ten and 15 minutes relative to a previously obtained calibration curve showing the ICG concentration in blood vs. absorbance thereby to calculate the blood plasma disappearance rate and the retention rate. In recent years, a method of changing the quantity of the ICG injection has been used to measure the blood plasma disappearance rate several times thereby to obtain an index expressing a quantity of a hepatic cell function $R_{MAX}$ (removed maximal).

Japanese Patent Publication Gazette No. 58649/1985 has already proposed a method of measuring the blood plasma disappearance rate and the retention rate without performing blood collections. According to that method, light is applied through the body surface of an organism, which in turn transmits light of a wavelength having a high ICG absorption sensitivity and light of a wavelength having substantially no ICG absorption sensitivity. The respective quantities of transmitted light are measured to obtain the blood plasma disappearance rate and the retention rate of the light quantities as a function of time (dye disappearance curve).

In the aforementioned first method requiring the taking of blood samples, it is necessary to correctly measure the blood collection time after the injection of the dye. However, the time has not been accurately measured in an actual test, and the operation for such measurement has been complicated. Further, the testee has been subject to substantial mental and physical burdens caused by the repeated taking of blood samples. In addition, the index $R_{MAX}$ method for measuring the blood plasma disappearance rate several times by changing the quantity of the ICG injection requires taking blood samples more than ten times, whereby the burdens on the testee are further increased.

According to the second measuring method without blood collection as disclosed in Japanese Patent Publication No. 58649/1985, the output of a sensor actually attached to an organism fluctuates under the influence of such factors as a blood flow disturbance caused by compression applied to a blood vessel, vibration of the organism being the object of measurement, pulsation in the organism, change of the blood volume in the vital tissue (the blood volume in each part in the vital tissue is changed by merely vertically moving an arm) etc. As a result correct dye disappearance curve cannot be obtained.

SUMMARY OF THE INVENTION

Accordingly, a principal object of the present invention is to provide a liver function testing apparatus and method which remains uninfluenced by such factors as blood flow disturbance, vibration of an organism, pulsation in the organism and change of the blood volume in the vital tissue, to enable correct measurements.

The present invention provides an apparatus for testing the function of a liver. The apparatus comprises light source means for exposing vital tissue to first light of a wavelength absorbed by specific dye which is dosed into blood of the vital tissue to be taken in and removed by the liver and second light of a wavelength not absorbed by the dye, photoelectric conversion means for outputting first and second photoelectric conversion signals corresponding to the first light and the second light applied to the vital tissue from the light source means and obtained from the vital tissue, sampling means for sampling the photoelectric conversion signals, decision means for deciding the coefficient of a linear regression expression between the first and second photoelectric conversion signals on the basis of variable components in the blood included in the sampled first and second photoelectric conversion signals and arithmetic means for operating a value correlated with specific dye concentration in the blood on the basis of a sampling signal during a prescribed period after a lapse of a predetermined time from an injection of the specific dye and the decided coefficient of the regression line expression.

In a preferred embodiment of such a liver function testing apparatus, a coefficient of a simulation function in the form of a function of time is obtained by using the method of least squares on the basis of the processed values correlated with the specific dye concentration.

In a further preferred embodiment of the present invention, a blood plasma disappearance rate of the specific dye is found on the basis of the obtained coefficient of the simulation function.

In yet another preferred embodiment of the present invention, a retention rate of the specific dye in a prescribed period is found on the basis of the obtained coefficient of the simulation function.

In a further embodiment of the present invention, an index expressing a quantity hepatic cell function $R_{MAX}$ is found on the basis of the obtained coefficient of the simulation function.

Thus, according to the present invention, a first light of a wavelength absorbed by a specific dye dosed into the blood of vital tissue, said dye to be taken in by and removed by the liver and a second light of a wavelength not absorbed by the dye, are applied to the vital tissue and first and second photoelectric conversion signals corresponding to the first light and to the second light are obtained from the vital tissue by sample. A coefficient of a regression line expression or relationship between the first and second photoelectric conversion signals, is determined on the basis of variable components in the blood as represented by the sampled first and second photoelectric conversion signals to perform a biocalibration. Thus, a value correlated with a specific dye concentration in the blood on the basis of sampling signals obtained during a prescribed period of time following an injection of the specific dye and the decided coefficient of the regression line expression are availabe for processing to obtain liver function testing results. Factors such as a blood flow disturbance, vibration and pulsation of an organism etc. when a sensor is attached to an organism can be removed by biocalibration, to process or calculate the value correlated with the specific dye concentration. Further, a correct time management of a disappearance curve of the specific dye has become possible, for obtaining correct data of the blood plasma disappearance rate, the retention rate, an index expressing the total amount of the hepatic cell function, etc. The present more correct data need not be based on several different blood samples as in conventional blood correction method. Rather, the present test results are based on a larger number of data of the disappearance curve, whereby the reliability of the results is improved.

These and other objects, features, aspects and advantages of the present invention will become more apparent from the following detailed description of the invention when taken in conjunction with the accompanying drawings.

BRIEF DESCRIPTION OF THE DRAWINGS

FIGS. 1 to 4 are diagrams for illustrating the principle of the present invention;

FIG. 6 illustrates the timing for detecting quantities of light of wavelengths $\lambda_1$ and $\lambda_2$ after passage through a prescribed optical path in a tested object;

FIGS. 8A to 8D are flow charts for concretely illustrating the operation of the embodiment of FIG. 5, in which FIG. 8A shows a data sampling subroutine, FIG. 8B shows a biocalibration mode, FIG. 8C shows an initialization mode and FIG. 8D shows a measurement mode;

FIG. 20 illustrates data stored in a RAM employed in another embodiment of the present invention;

Figure 2:
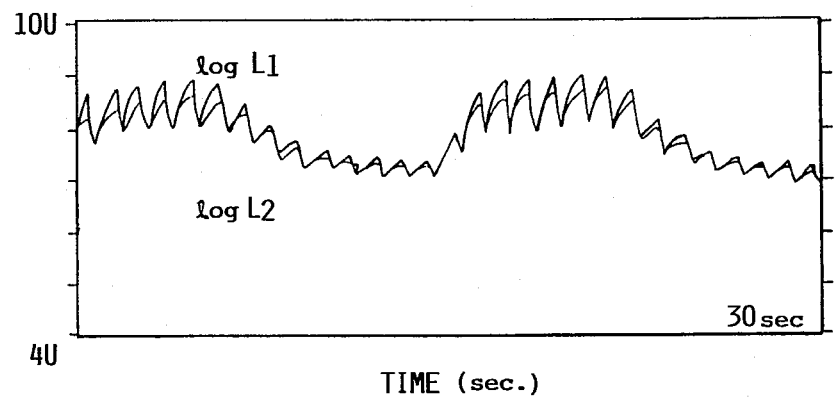

DETAILED DESCRIPTION OF PREFERRED EXAMPLE EMBODIMENTS AND OF THE BEST MODE OF THE INVENTION

Before explaining the embodiments of the present invention, the principle of the biocalibration employed in practicing the present invention will first be described with reference to FIGS. 1 to 4.

It is assumed that symbols $I_1$ and $I_2$ indicate quantities of light having a wavelength $\lambda_1$ which is largely absorbed by a specific dye and light of a wavelength $\lambda_2$ which is not absorbed by the specific dye incident upon vital tissue 15 to be tested. The symbols $L_1$ and $L_2$ indicate light quantities after passage through a prescribed optical path in the vital tissue 15 such as a patient's fingertip. The relationships between the incident light quantities $I_1$ and $I_2$ and the passing light quantities $L_1$ and $L_2$ after an injection of the specific dye, are as follows:

$$\log I_1/L_1 = kg_1 \cdot Cg \cdot Vb + f_1(Cb, Vb) + \gamma t_1 \quad (1)$$

$$\log I_2/L_2 = f_2(Cb, Vb) + \gamma t_2 \quad (2)$$

Respective coefficients and variables are shown in FIG. 1. Symbols $f_1$ and $f_2$ represent functions which are determined by blood characteristics at the wavelengths $\lambda_1$ and $\lambda_2$.

On the other hand, the relationships between the incident light quantities $I_1$ and $I_2$ and the passing light quantities $L_1$ and $L_2$ before injection of the specific dye are as follows:

$$\log I_1/L_1 = f_1(Cb, Vb) + \gamma t_1 \quad (3)$$

$$\log I_2/I_2 = f_2(Cb, Vb) + \gamma t_2 \quad (4)$$

Figure 3:
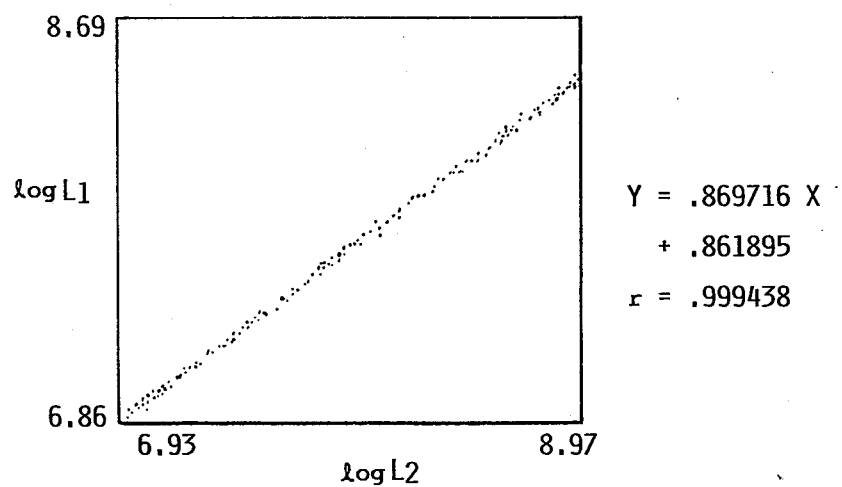

The relationships between the passing light quantities $L_1$ and $L_2$ prior to an actual injection of the specific dye, is measured as shown FIG. 2 and is a linear characteristic as shown in FIG. 3. These data are obtained by attaching a sensor to an organism and fluctuating the blood volume in the organism. It has been confirmed that such linearity has a reproducibility without any individual differences.

Then, the expressions (3) and (4) would appear as follows:

$$\log L_1 = A \log L_2 + B \quad (5)$$

That is, the same can be expressed as follows, by using the expressions (3) and (4):

$$\log I_1 - \{f_1(Cb, Vb) + \gamma t_1\} = A[\log I_2 - \{f_2(Cb, Vb) + \gamma t_2\}] + B \quad (6)$$

where Cb represents the blood concentration in a sample and Vb represents the blood volume of the sample.

A function C obtained by multiplying the concentration of the specific dye by the blood volume in the sample and the absorption coefficient of the specific dye by using the expressions (1) and (2) after injection of the specific dye, can be expressed as follows:

$$C = \log L_1 - [A \log L_2 + B] \quad (7)$$

The function C of the expression (7) is found as follows:

$$C = \log I_1 - kg \cdot Cg \cdot Vb - f_1(Cb, Vb) + \gamma t_1 - A[\log I_2 - \{f_2(Cb, Vb) + \gamma t_2\}] - B \quad (8)$$

Through the expression (6), we have:

$$C = -kg \cdot Cg \cdot Vb \quad (9)$$

Hence, it is understood that a signal of the function C can be obtained by using FIG. 3 as a biocalibration curve.

As to the function C, however, although the coefficient kg is constant, it can be considered that the blood volume Vb in each part changes from time to time, and hence, if the blood volume Vb in a prescribed sample created by the sensor once it is attached, is changed, the amount of the specific dye is also changed in proportion thereto, however the dye concentration remains unchanged. This is typically shown in FIG. 4.

Figure 4:
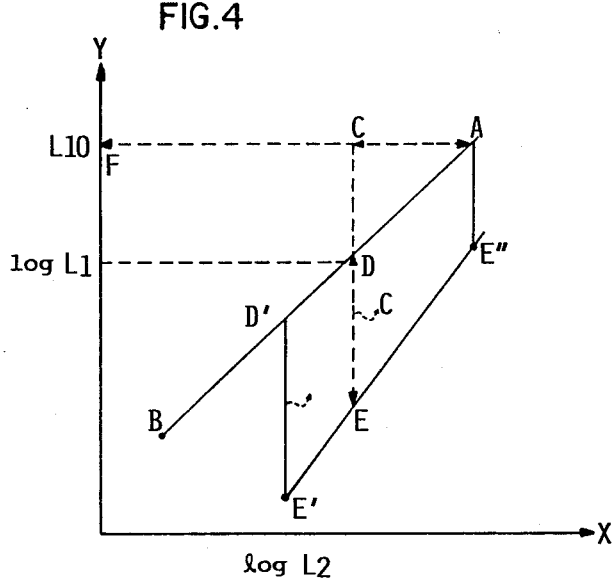

Referring to FIG. 4, it is assumed that $\overline{DE}$ represents the value of the function C after a lapse of $t_1$ minutes. The blood contained in the prescribed sample obtained after a lapse of $t_1 + \Delta t$ minutes is changed in volume, whereby the observation point is changed from E to E'. Assuming that $\Delta t$ is sufficiently less than one minute, the specific dye concentration in the blood after the lapse of $t_1$ minutes may be considered identical to that after the lapse of $t_1 + \Delta t$ minutes. However, as to the function C, the change is from $C = \overline{DE}$ to $C' = \overline{D'E'}$. $C \neq C'$, and hence some correction must be made. Hence, by normalizing $\overline{DE}$ and $\overline{D'E'}$ at the point $L_{10}$, an apparent fluctuation of the dye concentration due to the fluctuation of the blood volume can be corrected. When the specific dye is injected, a signal of only $\log L_1$ changes to a point E, for example. At this time, $\overline{DE}$ becomes the function C as shown in the expression (9). The blood volume Vb in the expression (9) can be interpreted as being denoted by $\overline{CD}$, and hence, normalizing the Y coordinate of a point A as $L_{10}$, the same is expressed as follows:

$$Vb \, \alpha 1 + \frac{\log L_{10} - (A \cdot \log L_2 + B)}{\log L_{10}} \quad (10)$$

Hence, a signal Cg corresponding to the specific dye concentration can be found by the expressions (7) and (10) as follows:

$$Cg = \frac{\log L_{10} - (A \cdot \log L_2 + B)}{1 + \frac{\log L_{10} - (A \cdot \log L_2 + B)}{\log L_{10}}}$$

$$= \frac{\log L_{10}[\log L_1 - (A \cdot \log L_2 + B)]}{2\log L_{10} - (A \cdot \log L_2 + B)} \quad (11)$$

Using the method of least squares, the function Cg of a simulation curve representing a time change of the aforementioned result Cg as calculated is expressed as follows:

$$Cg = Ae^{Bt} \quad (12)$$

where t represents the elapsed time after injection of the specific dye and symbols A and B represent constants.

The constants A and B are found by the above expression (12). The blood plasma disappearance rate k and the T-minute retention rate R % are expressed as follows:

$$k = -B \quad (13)$$

$$R\% = e^{BT} \quad (14)$$

where T represents the elapsed time after injection characteristically expressing the intake of the specific dye into the liver.

Figure 5:
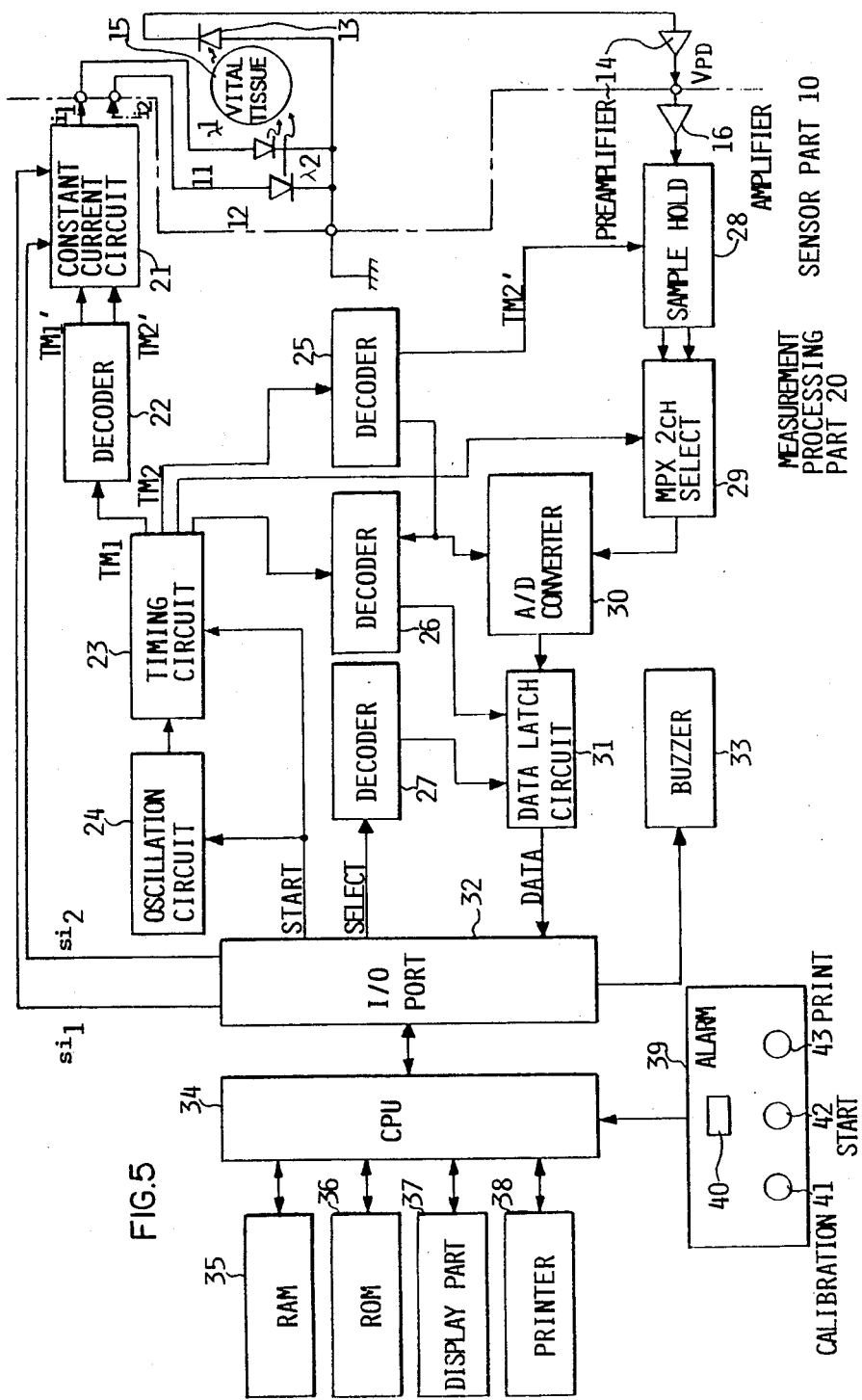
FIG. 5 is a schematic block diagram showing the structure of an embodiment of the present invention.

An embodiment of the present invention employing the aforementioned biocalibration, will now be described with reference to FIG. 5 showing a schematic block diagram.

The liver function testing apparatus of FIG. 5 comprises a sensor part 10 and a measured signal processing part 20. The sensor part 10 includes a first light source 11, a second light source 12, a light receiving element 13 and a preamplifier 14. The first light source 11 and the second light source 12 generate optical pulses of a wavelength $\lambda_1$ having a large absorbance to a specific dye and optical pulses of a wavelength $\lambda_2$ having no absorbance, respectively. The light receiving element 13 receives light applied to vital tissue 15 from the light sources 11 and 12 to pass through a prescribed optical path. The light sources 11 and 12 are energized by the measurement processing part 20 to alternately emit light by pulse operation, respectively.

The measurement processing part 20 includes a CPU 34 which operates as an arithmetic means. The CPU 34 supplies a start signal to an oscillation circuit 24 and a timing circuit 23 through an I/O port 32. The oscillation circuit 24 regularly oscillates to produce a prescribed clock signal. This clock signal and the aforementioned start signal are utilized to supply constant currents $i_1$ and $i_2$ to the first light source 11 and to the second light source 12 from a constant current circuit 21 through the timing circuit 23 and a decoder 22 at timings $TM_1'$ and $TM_1''$ in FIG. 6.

The light emitted by the first light source 11 and the light emitted by the second light source 12 pass through the prescribed optical path in the vital tissue 15, to be incident upon the light receiving element 13. A current generated by the light receiving element 13 is supplied to the preamplifier 14 for a current-to-voltage conversion and amplification for further processing in the measurement processing part 20. The output of the preamplifier 14 is amplified to a level within a prescribed range by an amplifier 16 provided in the measurement processing part 20, whereby an output such as $V_{PD}$ in FIG. 6 is obtained. A sample and hold circuit 28 samples and holds the output from the amplifier 16 on the basis of a timing signal $TM_2'$, shown in FIG. 6, generated by the timing circuit 23 and a decoder 25.

The signal thus sampled and held is selected by a multiplexer 29 and converted into a digital signal by an A-D converter 30, to be data-latched by a data latch circuit 31. At this time, the multiplexer 29, the A-D converter 30 and the data latch 31 are synchronized by the timing circuit 23 and the decoder 26.

Figure 7:
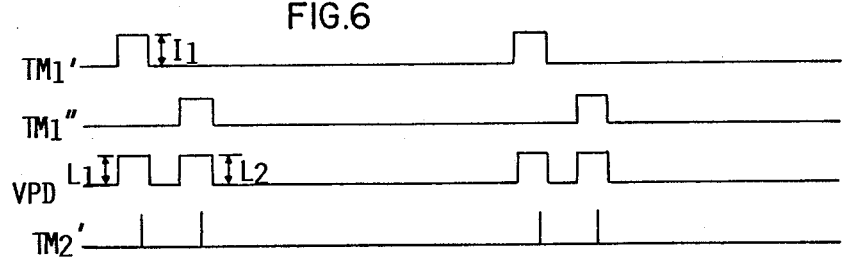
FIG. 7 illustrates data stored in a RAM as shown in FIG. 1.

The latched data are timed by a decoder 27 through a select signal outputted from the CPU 34 through the I/O port 32, to be stored in a RAM 35 as digital signal $L_1$ and $L_2$. The I/O port 32 is connected to a buzzer 33, which informs an operator regarding the timing for injecting the specific dye. Further, the CPU 34 is connected with the RAM 35, a ROM 36, a display 37 and an operation part 28. The RAM 35 is adapted to store data as shown in FIG. 7 as will be described, below and the ROM 36 stores programs based on flow charts as shown in FIGS. 8A to 8D to be described below. The display 37 displays data as shown in FIGS. 9 to 12, as hereinafter described. A printer 38 prints the result of a liver function test.

The function part 39 includes an alarm LED 40, a calibration key 41, a start key 42 and a print key 43. The alarm LED 40 causes an alarm when the reliability of the test result is small and the calibration key 41 is used to set a biocalibration mode, while the start key 42 is used to start a measurement mode and the print key 43 is used to cause a printout of the test result.

In the aforementioned exemplary structure as shown in FIG. 5, the light emitted by the first and second light sources 11 and 12 and caused to pass through the prescribed optical path in the vital tissue 15 is received by a single light receiving element 13. However, the present method is not restricted to the use of a single light sensor but light receiving elements may be provided in correspondence to the first and second light sources 11 and 12, respectively, for sampling outputs of the respective light receiving elements, thereby to read the respective sampling outputs by the CPU 34 in a time-sharing manner. Alternatively, a single light source commonly emitting light having a wavelength $\lambda_1$ absorbed by specific dye and light having a wavelength $\lambda_2$ not absorbed by the same may be provided as light source means, with provision of two filters for individually transmitting the light of the respective wavelengths and light receiving elements corresponding to the respective filters would be used.

With reference to FIGS. 5, 8A to 8D and 14, an actual operation sequence of an embodiment of the present invention will now be described.

The operation of the inventive apparatus includes a data sampling mode, a biocalibration mode, an initialization mode and a measurement mode, and FIGS. 8A, 8B, 8C and 8D show operation flow charts for these modes, respectively.

Figure 8A:
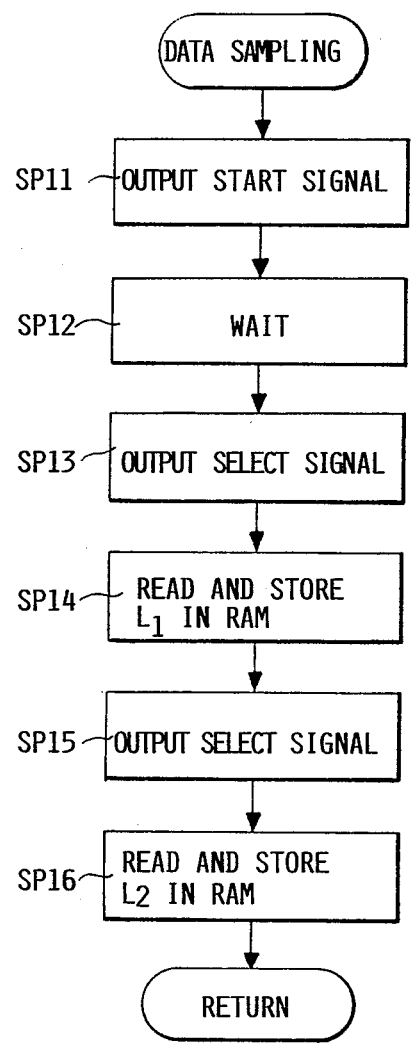

First, it is pointed out that the data sampling mode as shown in FIG. 8A is executed as subroutines in the calibration mode and the measurement mode as hereinafter described. Steps (abbreviated as SP in the figures) SP11 to SP16 are adapted to sample quantities of light of a pair of wavelengths $\lambda_1$ and $\lambda_2$ after passage through a measured object and store the same in the RAM 35. Namely, the CPU 34 outputs the start signal from a line as shown in FIG. 5 through the I/O port 32 at the step SP11. The values $L_1$ and $L_2$ are data-latched by the start signal, as hereinabove described. The CPU 34 waits until the data are latched at the step SP12.

Then, at the step SP13, the CPU 34 outputs the select signal to a select line as shown in FIG. 5 through the I/O port 32, to read the data of $L_1$ through the I/O port 32 at the step SP14, thereby to store the same in a storage area $8a1$ of the RAM 35 as shown in FIG. 7.

Similarly, the CPU 34 stores the data of $L_2$ in a storage area $8a2$ of the RAM 35 at the steps SP15 and SP16.

Upon completion of the aforementioned operation or processing at the step SP16, the CPU 34 returns to the original step. This will be described with reference to FIG. 8B showing the biocalibration mode and FIG. 8D showing the measurement mode.

Figure 8B:
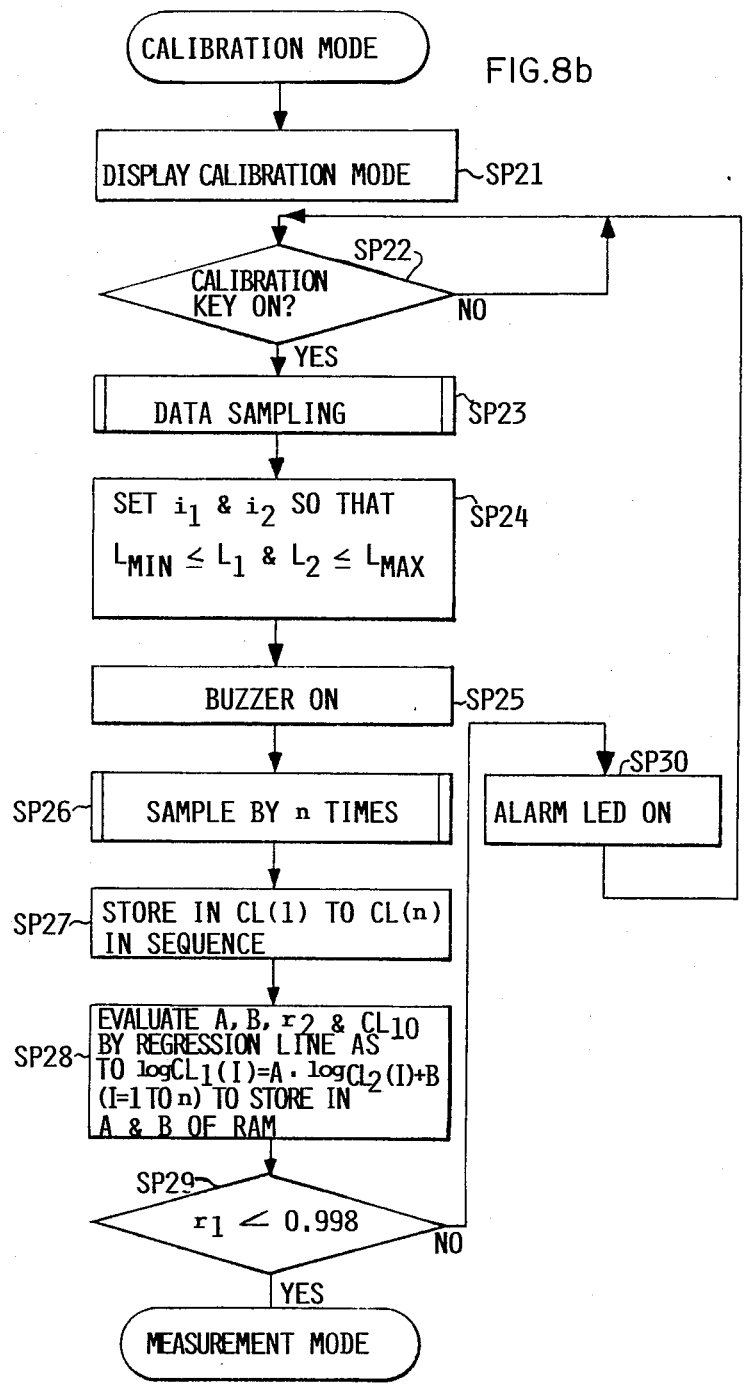
Figure 8C:
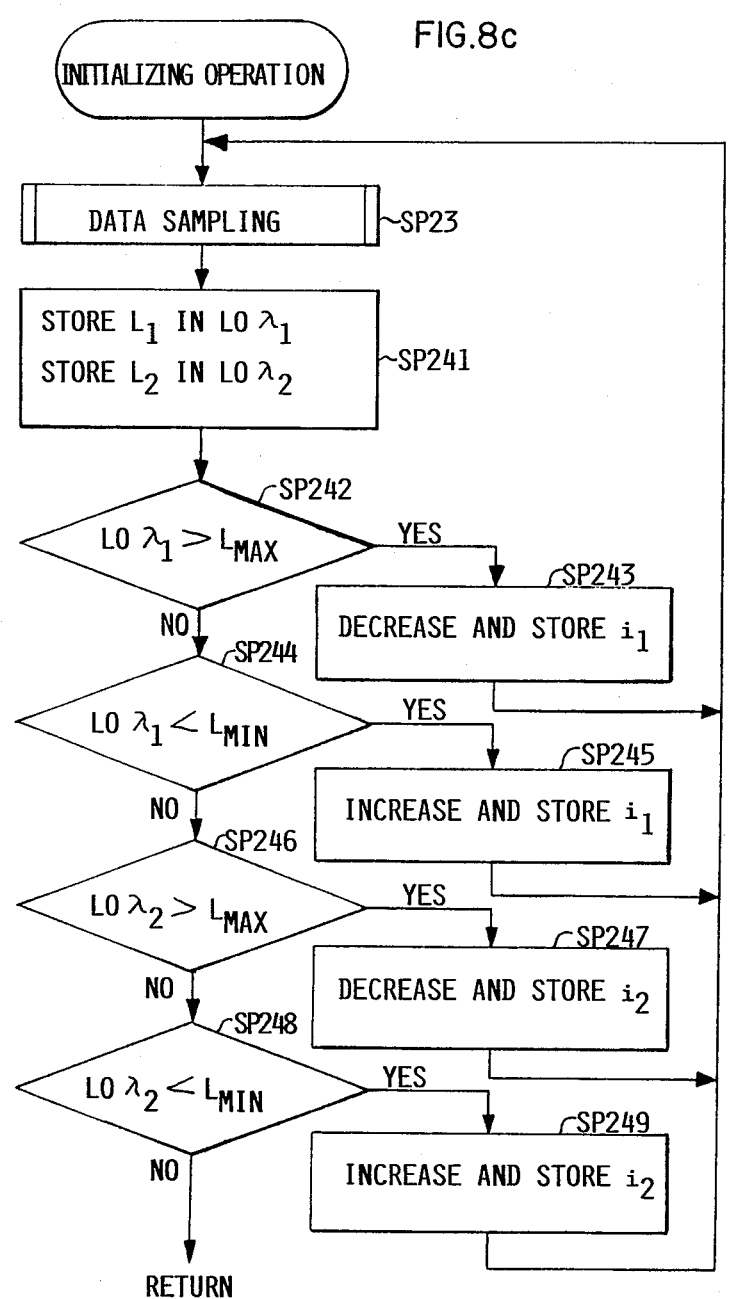
Figure 8D:
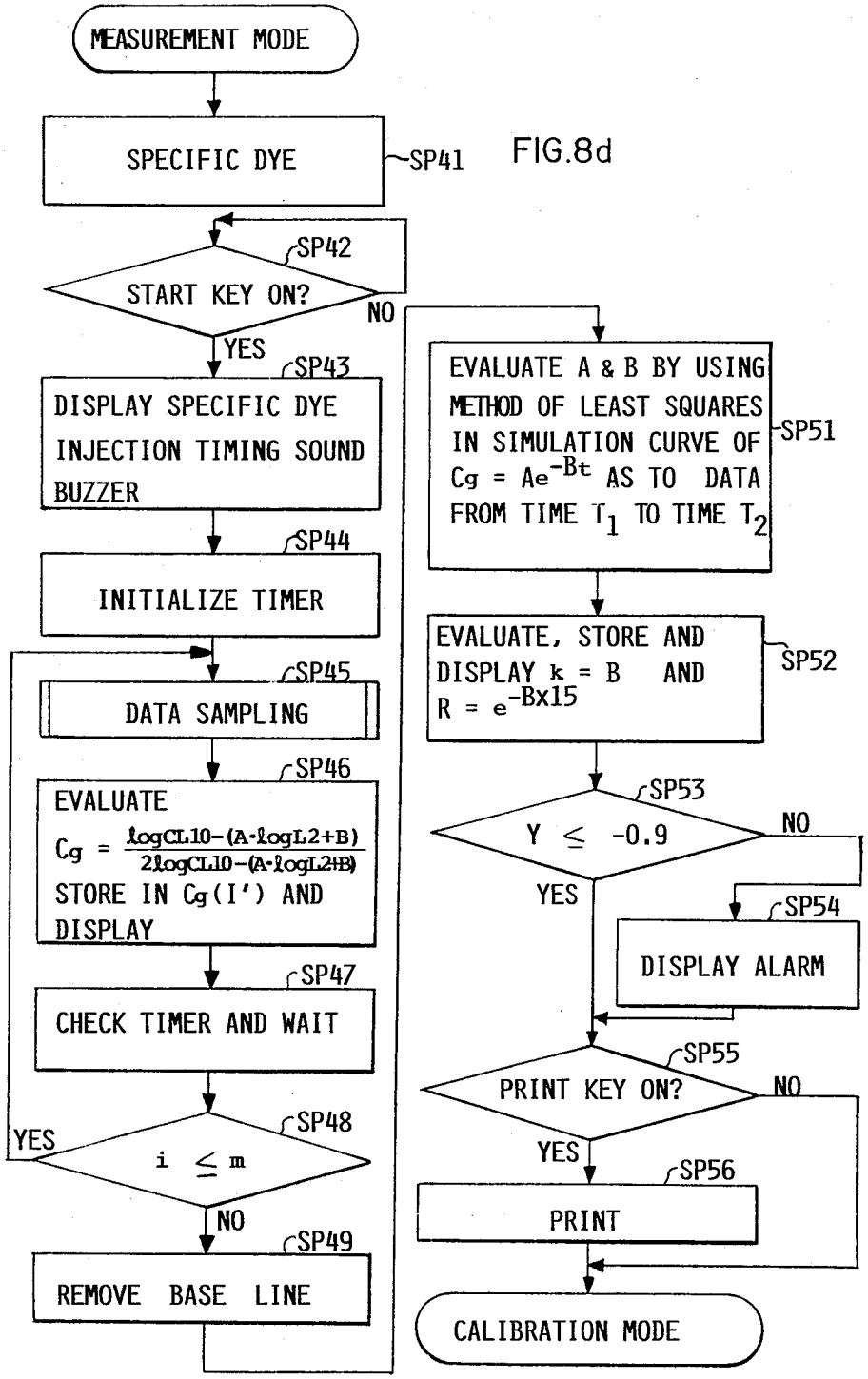
Figure 9:
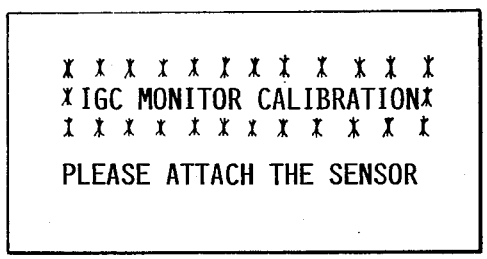
FIGS. 9 to 12 are illustrative of exemplary displays on a display device shown in FIG. 5.

FIG. 8B shows the operation flow chart of the biocalibration mode, which is started upon power supply to the apparatus or upon completion of the operation of the measurement mode as shown in FIG. 8D, as hereinafter described. At a step SP21, the CPU 34 causes the biocalibration mode to appear on the display 37 and indicates that the sensor part 10 should be attached to a patient as shown in FIG. 9, for example. In accordance with this indication, an operator attaches the sensor part 10 to the vital tissue 15.

Thereafter the CPU 34 waits until the calibration key 41 is operated at a step SP22. When the calibration key 41 has been operated, the CPU 34 advances to a step SP23, to execute the data sampling subroutine as shown in FIG. 8A, as described above.

Then, the CPU 34 controls the constant current circuit 21 as shown in FIG. 5 so that the data $L_1$ and $L_2$ read at the step SP23 are within ranges of the light quantity data $L_{MAX}$ and $L_{MIN}$ stored in storage areas $8b1$ and $8b2$ of the RAM 35. The CPU 34 then stores current set values $i_1$, $i_2$ in storage areas $8c1$ and $8c2$ in the RAM 35. Thereafter the currents $i_1$, $i_2$ regularly flow to the light sources 11 and 12. Starting the operation for causing the aforementioned currents will be described in further detail with reference to FIG. 8C.

Then, the CPU 34 sounds the buzzer at a step SP25, to inform that power setting is completed. Subsequent steps SP26 to SP29 are shown in the flow chart for performing the aforementioned biocalibration. More specifically, the CPU 34 samples the values of $L_1$ and $L_2$ n times respectively at the steps SP26 and SP27, to cause $CL_1(1)$ to $CL_1(n)$ to be stored in storage areas $8d1$ to $8dn$ and $CL_2(1)$ to $CL_2(n)$ stored in storage areas $8e1$ to $8en$. At the subsequent step SP28, the CPU 34 performs a regression line analysis with respect to log $CL_1(I)$ and log $CL_2(I)$ (I=1 to n), in accordance with the following operation expression:

$$\log Cl_1(I) = A \log CL_2(I) + B$$

The CPU 34 finds the values A and B in the above operation expression, a correlation coefficient $r_1$ and the maximum value of $CL_1(I)$, (I=1 to n) as $CL_{10}$, to store the same in storage areas $8f1$, $8f2$, $8f3$ and $8f4$ in the RAM 35, respectively.

Then, at the step SP29, the CPU 34 determines whether or not the correlation coefficient $r_1$ is at least 0.998 in order to verify the reliability of the biocalibration, and advances to a step SP30 if the same is less than 0.998 to light the alarm LED 40, and returns to the step SP22 to again perform biocalibration. On the other hand, if a determination is made that the correlation coefficient $r_1$ is at least 0.998, the CPU 34 advances to the measurement mode as shown in FIG. 8D. The reference value 0.998 of the correlation coefficient $r_1$ herein employed is a mere example, which is determined based on the performance of the entire apparatus. During the data sampling by n times at the step SP26, the testee raises and brings down his hand and compresses the same by the sensor, in order to change the blood volume in the hand.

With reference to FIG. 8C, the aforementioned initializing operation at the step SP24 as shown in FIG. 8B will now be described in more detail.

The light quantity data $L_1$ and $L_2$ of the light of the wavelengths $\lambda_1$ and $\lambda_2$ are stored in the storage areas $8a1$ and $8a2$ of the RAM 35. At a step SP241, the CPU 34 stores the values of $L_1$ and $L_2$ in storage area $8h1$ and $8h2$ in the RAM 35 as $L0\lambda_1$ and $L0\lambda_2$, respectively. Then the CPU 34 executes steps SP242 to SP249, to adjust the set values of the currents flowing from the constant current circuit 21 so that $L0\lambda_1$ and $L0\lambda_2$ are set between the light quantity data $L_{MAX}$ and $L_{MIN}$ ($L_{MAX} > L_{MIN}$) stored in the storage areas $8b1$ and $8b2$ of the RAM 35.

More specifically, if $L0\lambda_1$ is greater than $L_{MAX}$ at the step SP242, the CPU 34 advances to the step SP243 to set the current set value $i_1$ at a small value to again execute the steps SP23 and SP241, and a determination is again made as to whether or not $L0\lambda'_1$ is greater than $L_{MAX}$ at the step SP242. If $L0\lambda_1$ is less than $L_{MAX}$, the CPU 34 advances to the step SP244 to determine whether or not $L0\lambda_1$ is less than $L_{MIN}$. If $L0\lambda_1$ is less than $L_{MIN}$, the CPU 34 increases the value of the current set value $i_1$ at the step SP245, to return to the aforementioned step SP23. This operation is repeated to set the current value $i_1$ so that $L0\lambda_1$ is between $L_{MAX}$ and $L_{MIN}$.

Then, at the steps SP246 to SP249, the current value $i_2$ is set so that $L0\lambda_2$ is between $L_{MAX}$ and $L_{MIN}$, similarly to the steps SP242 to SP245. Thus, the current values $i_1$ and $i_2$ finally set at the steps SP23 to SP249, are stored in the storage areas $8c1$ and $8c2$ of the RAM 35.

Figure 10:
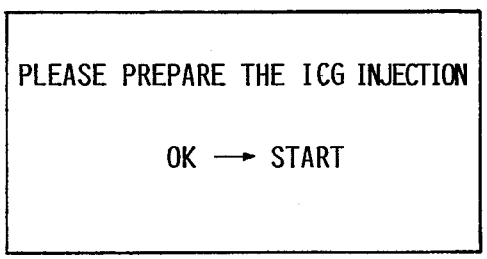
Figure 11:
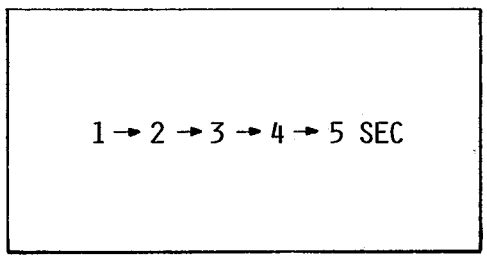

The measurement mode will now be described with reference to FIG. 8D. At a step SP41, the CPU 34 alerts the operator by an indication on the display 37, to inject the specific dye into the patient, for example, an ICG injection as shown in FIG. 10. The operator prepares the injection of the specific dye and at step SP42, the CPU 34 waits until the start key 42 is operated. Upon a determination that the start key 42 has been operated, the CPU 34 displays a timing for the injecting of the specific dye at a step SP43, while sounding the buzzer 33. This operation is displayed as $1\rightarrow 2\rightarrow 3\rightarrow 4\rightarrow 5$ as shown in FIG. 11, for example, so that the measurer injects the specific dye upon display of "5". The CPU 34 generates a first sound from the buzzer 33 with the displays of "1", "2", "3" and "4", while generating a different sound from the buzzer 33 upon display of "5".

Upon generation of the sound and the display, the measurer injects the specific dye. The CPU 34 sets "0" as the initial value of a timer at a step SP44. Then, at a step SP45, the CPU 34 executes a data sampling program, which is the subroutine as described above with reference to FIG. 8A. Then, the sampling data are stored in the storage areas $8a1$ to $8a2$ of the RAM 35 as $L_1$ to $L_2$, respectively. At a step SP46, the CPU 34 performs an operation based on the following operation expression by using the coefficients A, B, and $L_{10}$ stored in the storage areas $8f1$, $8f2$ and $8f4$ of the RAM 35 in the biocalibration mode as described above with reference to FIG. 8B, to store Cg(I) in a storage area $8g1$ of the RAM 35:

$$Cg(I) = \frac{\log CL_{10}[\log L_1(I) - (A \cdot \log L_2(I) + B)]}{2\log CL_{10} - (A \cdot \log L_2(I) + B)}.$$

Figure 12:
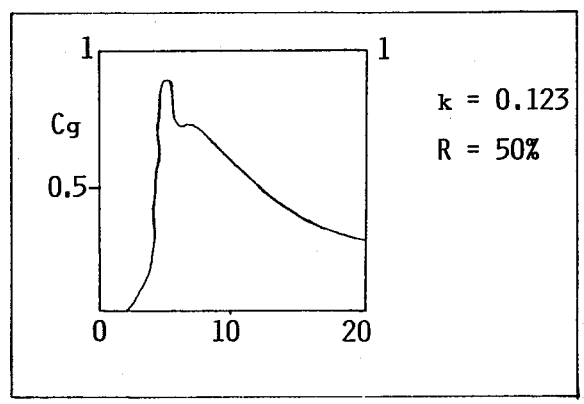

The value of Cg(I) is displayed on the display 37 at the step SP46 in a mode as shown in FIG. 12, for example. Referring to FIG. 12, the abscissa indicates the elapsed time from the injection of the specific dye and the ordinate indicates the value of Cg(I). Assuming that m represents the sampling number of a disappearance curve of the specific dye, symbol I indicates integers 1 to m, and assuming that $T_s$ represents a measuring time of the disappearance curve, a single sampling time is $ITM = T_s/(m-1)$. The same coincides with the injection time of the specific dye in the case of $I = 1$. At a step SP47, the CPU 34 waits during this sampling time ITM.

Figure 13:
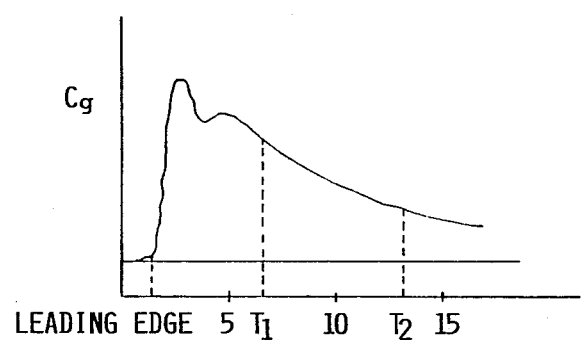
FIG. 13 shows an example of a disappearance curve of a specific dye as measured in accordance with the present invention.

Upon a lapse of this standby time, the CPU 34 judges whether or not i is greater than m at a step SP48. The CPU 34 advances to a step SP49 if i is greater than m, while the same again returns to the step SP45 to repeat sampling if i is less than the m. The data Cg(I) stored in the storage areas $8g1$ to $8gm$ of the RAM 35 draw a disappearance curve of the specific dye as shown in FIG. 13, for example, and the leading edge thereof is detected so that data preceding thereto are subtracted as baselines from the respective values of Cg(I), to be again stored in the storage areas $8g1$ to $8gm$. $L_1$ to $L_2$ at the step SP45 may be average values of k times, in order to improve the accuracy of the measurement.

Then, at a step SP51, the CPU 34 finds the constants A and B by using the method of least squares in a simulation curve of:

$$Cg(I) = Ae^{Bt} \text{ wherein}$$

$$I = T_s/(m-1)(\min.)$$

with respect to data between times $T_1$ to $T_2$ $(0 < T_1 < T_2 < T_s)$ within the data Cg(I) stored in the storage areas $8g1$ to $8gm$.

Then, the CPU 34 performs an operation to evaluate the blood plasma disappearance rate $k = -B$ and the T-minute retention rate $R \% = e^{BT}$ at a step SP52. The values k and R % thus evaluated are stored in storage areas $8j1$ and $8j2$ of the RAM 35, respectively. At this time, the CPU 34 determines a correlation coefficient $r_2$ by the method of least squares and stores the correlation coefficient $r_2$ in a storage area $8j3$ of the RAM 35. The CPU 34 further generates an end sound from the buzzer 33.

Further, the CPU 34 causes the values k and R % to appear on the display 34 in a mode as shown in FIG. 12, for example. Then, at a step SP53, the CPU 34 determines whether or not the correlation coefficient $r_2$ is less than 0.95, for example. This determination is made to check the degree of correlation since the correlation is improved as the correlation coefficient $r_2$ approaches $-1$. The value $-0.95$ is provisionally selected between zero and $-1$, and the reliability of the apparatus is improved as the value comes closer to $-1$.

If the correlation coefficient $r_2$ is greater than 0.95, for example, the CPU 34 determines that the reliability is insufficient and this is indicated by switching on the alarm LED 40 at the step SP54. On the other hand, if the correlation coefficient $r_2$ is less than $-0.95$, for example, at the step SP53, the CPU 34 advances to a step SP55 without flashing the alarm LED 44, since the measurement is reliable. At the step SP55, the CPU 34 determines whether or not the print key 43 is operated, to cause the printer 38 to print the values k and R % if the determination is YES.

If necessary, the CPU 34 also causes the printing of dye disappearance curves of Cg(I) stored in the storage areas $8g1$ to $8gn$ of the RAM 35 and it may cause an advance to the biocalibration mode as shown in FIG. 8B. When a determination is made that the print key 43 has not been operated at the step SP55, the CPU 34 advances to the calibration mode.

Figure 14:
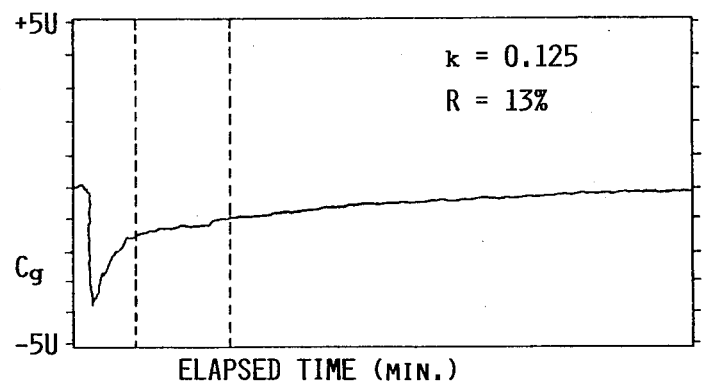
FIG. 14 shows the specific dye concentration Cg as a function of time as measured according to the invention for parameters k=0.125 (blood plasma disappearance rate) and R=13% (15 minute retention rate).
Figure 15:
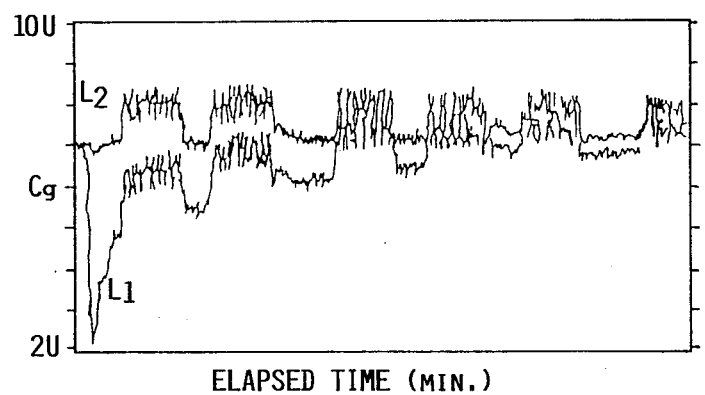
FIG. 15 illustrates light quantity data $L_1$ and $L_2$ as a function of time.

FIG. 14 shows the result of a measurement experiment in the liver function testing apparatus as shown in FIG. 5. The sensor part 10 was attached on a left fingertip of a male patient having hepatic disease (age: 60, weight: 48 Kg). An aqueous containing 24 mg of ICG (0.5 mg per Kg) was intravenously injected into the vein at the vein of his right elbow. FIG. 15 shows the time change of $L_1$, $L_2$ where a light emitting diode emitting light at a wavelength $\lambda_1 = 810$ nm is used as the first light source 11 and a light emitting diode emitting light at a wavelength $\lambda_2 = 940$ nm is used as the second light source 12.

The value k calculated on the basis of the ICG disappearance curve was 0.125 as shown in FIG. 14 and the value R % was 13%, while the value k measured by the conventional blood collection method was 0.124 and the value R % was 12.8%, showing a substantial coincidence. FIG. 15 also shows raw data of $L_1$ and $L_2$. It is clearly understood from FIG. 14 that the blood volume in the organism fluctuated.

FIGS. 16 to 19 show results of experiments for illustrating the effects attained by the present invention.

Figure 16:
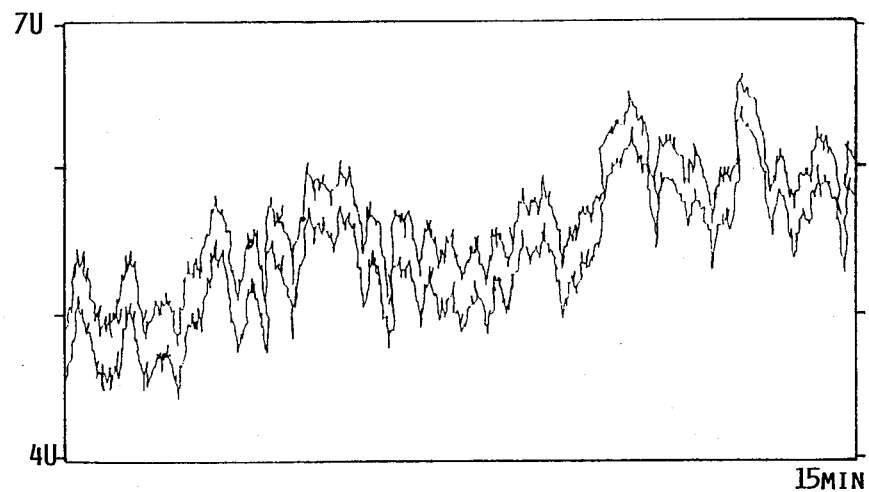
FIGS. 16 to 19 are diagrams for illustrating effects obtained by practicing the present invention.
Figure 17:
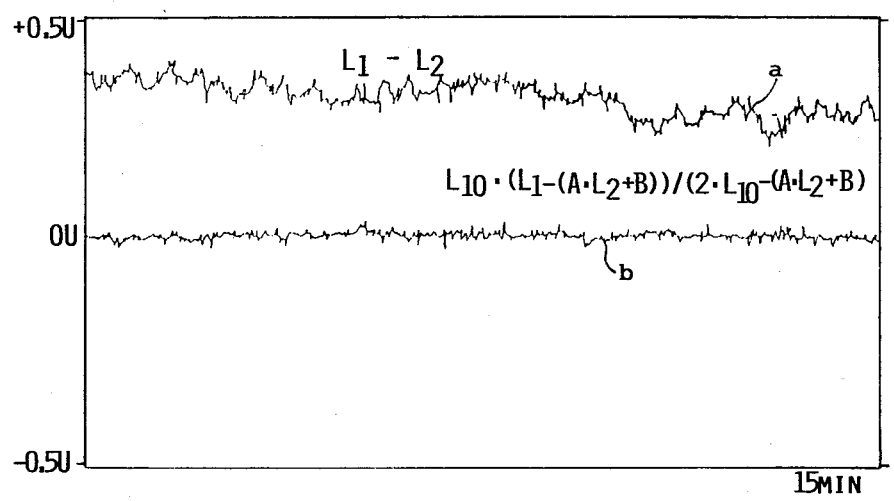

FIG. 16 shows time changes for 15 minutes in intensity levels of the first light and the second light passing through the vital tissue 15 from the light sources 11 and 12 while bringing the vital tissue 15 in a rest state. Merely finding difference ($L_1 - L_2$) between the first light and the second light, the base line largely fluctuated as characteristic a in FIG. 17. When the fluctuation of the blood volume is corrected by the biocalibration according to the present invention, the base line is substantially stable as shown by characteristic b in FIG. 17.

Figure 18:
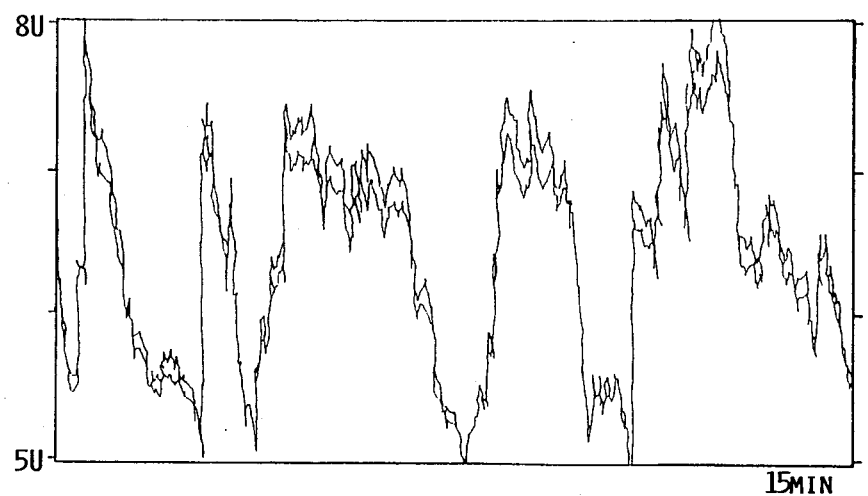
Figure 19:
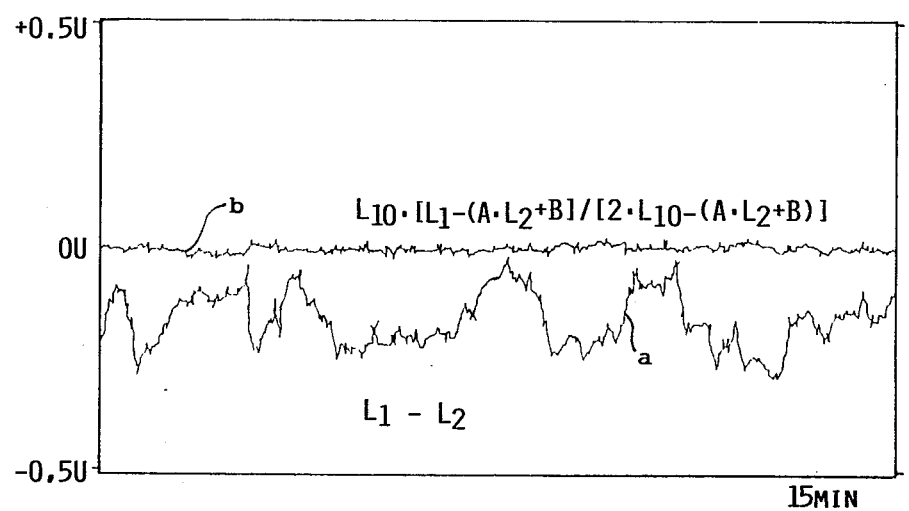

FIG. 18 shows time changes for 15 minutes in intensity levels of the first light and the second light passing through the vital tissue 15 from the light sources 11 and 12 when the testee's body is moved to cause a blood volume fluctuation. An evaluation of the difference between the first light and the second light with such a large fluctuation, show that the base line fluctuates substantially as shown by characteristic a in FIG. 19. When the fluctuation of the blood volume is corrected by the biocalibration according to the present invention, the base line is substantially stabilized as shown by characteristic b in FIG. 19.

In the aforementioned embodiment, the present invention is applied to the case of evaluating the coefficient of the simulation function by using the method of least squares on the basis of the value correlated with the specific dye concentration in the blood for evaluating the blood plasma disappearance rate k and the retention rate R %. However, the present invention is not restricted to this but further applicable to the case of obtaining index $R_{MAX}$ on the basis of the aforementioned coefficient as obtained. Description is now made on such an embodiment with reference to FIG. 20 illustrating data stored in a RAM provided in an apparatus for measuring the index $R_{MAX}$.

The apparatus for measuring the index $R_{MAX}$ is identical in structure to that shown in FIG. 5, but the RAM 35 is provided with storage areas $8k1$ to $8k6$ and $8l1$ and $8l2$ as shown in FIG. 20, in place of the storage areas $8j1$ to $8j3$ as shown in FIG. 7.

Figure 21A:
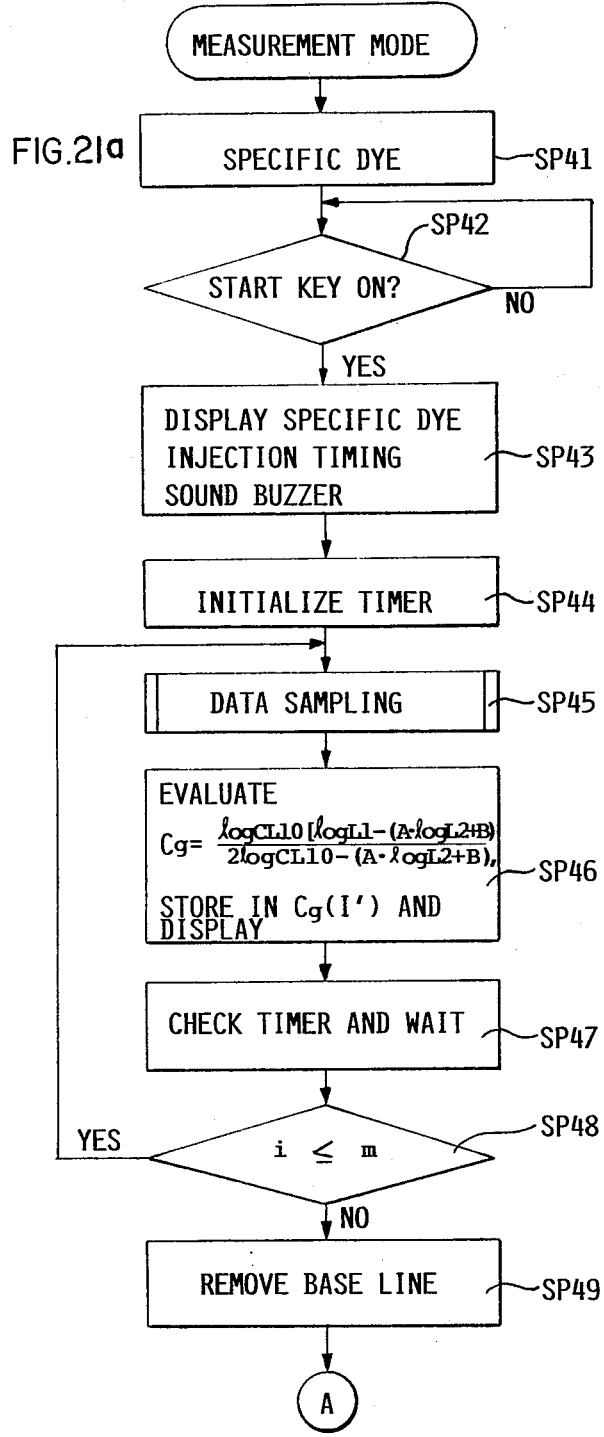
FIGS. 21A and 21B are flow charts for illustrating the operation of a measurement mode in another embodiment of the present invention.
Figure 21B:
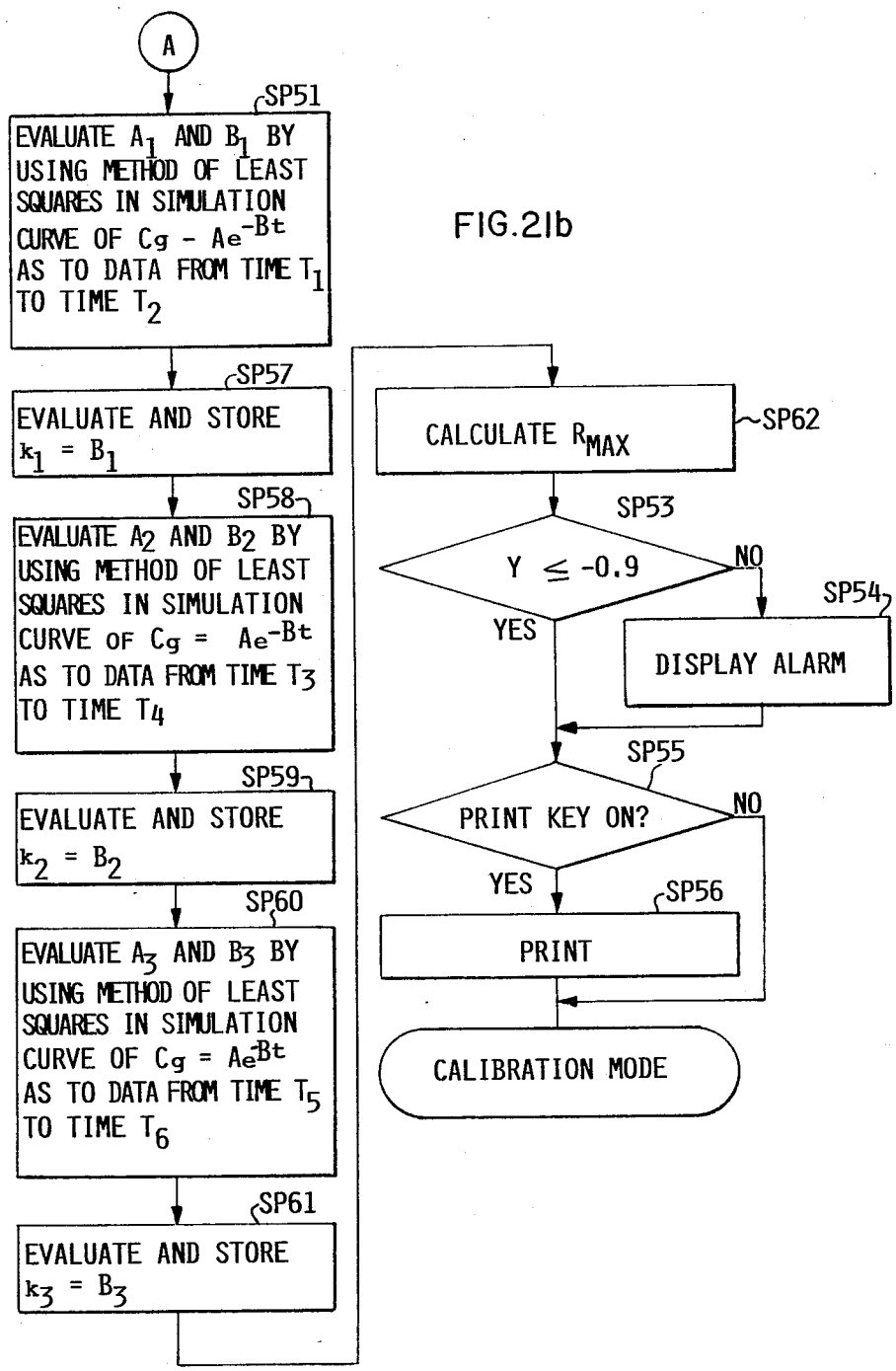

A data sampling mode in measuring the index $R_{MAX}$ is identical to that shown in FIG. 8A and a biocalibration mode is identical to that shown in FIG. 8B. The initializing operation or processing is identical to that shown in FIG. 8C. Within the operation or processing of the measurement mode as shown in FIGS. 21A and 21B, steps SP41 to SP51 and SP53 to SP56 are identical to those shown in FIG. 8D, and hence will not be described again.

Figure 22:
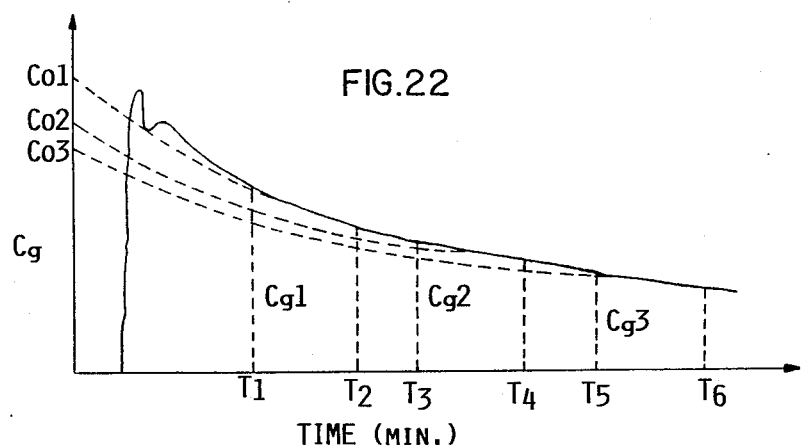
FIGS. 22 to 24 are diagrams for illustrating operation of another embodiment of the present invention.

In order to measure the index $R_{MAX}$, it is necessary to to process the data in accordance with simulation curves representing a time change of results of the operation or processing in at least two or more blocks by using the method of the least squares, to evaluate coefficients K of specific dye as to respective blocks on the basis of the functions, as shown in FIG. 22.

Then, at a step SP51, the CPU 34 determines the constants $A_1$ and $B_1$ in a block between times $T_1$ to $T_2$, similarly to the above embodiment. At a step SP57, the CPU 34 evaluates $K_1$ from $K_1 = B_1$ while evaluating a correlation coefficient $r_{g1}$, to store the same in the storage areas as $8k1$ and $8k2$ of the RAM 35. Similarly, the CPU 34 evaluates constants $A_2$ and $B_2$ in a block between times $T_3$ and $T_4$ at a step SP58, and evaluates a coefficient $K_2$ and a correlation coefficient $r_{g2}$ at a step SP59 to store the same in the storage areas $8k3$ and $8k4$. The CPU 34 further determines constants $A_3$ and $B_3$ at a step SP60 and evaluates a coefficient $K_3$ and a correlation coefficient $r_{g3}$ at a step SP61, to store the same in the storage areas $8k5$ and $8k6$. Then the CPU 34 operates determines the index $R_{MAX}$ at a step SP62.

Figure 23:
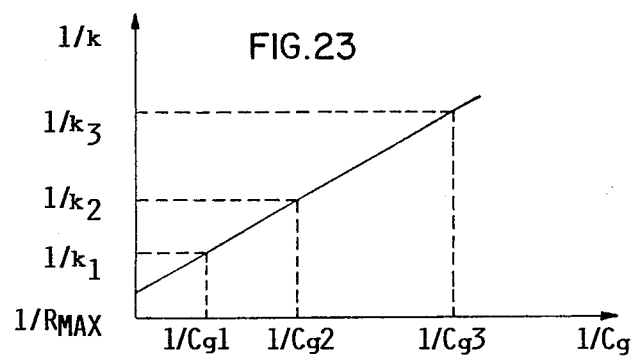
Figure 24:
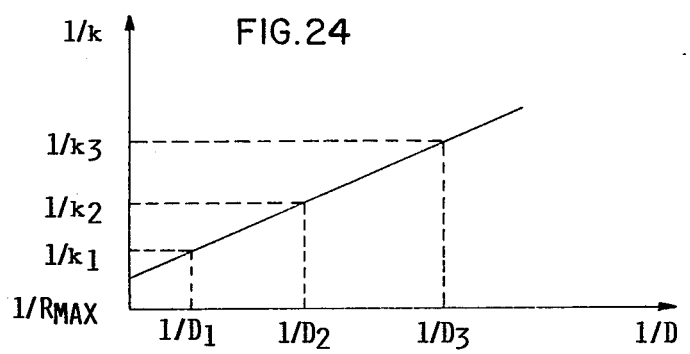

The times $T_1$ to $T_6$ and the coefficients $K_1$ to $K_3$ are slotted as shown in FIG. 22. The CPU 34 assumes that $C_{g1}$, $C_{g2}$ and $C_{g3}$ represent values corresponding to specific dye concentration values at the times $T_1$, $T_3$ and $T_5$, to display the graph as shown in FIG. 23. Referring to FIG. 23, the abscissa indicated $1/C_g$ and the ordinate indicated $1/K$. On the basis of these data, the CPU 34 processes a and b by using the method of least squares, through the following operational expression:

$$1/K_i = a(1/C_i) + b$$

$(i = 1, 2 \ldots m, m \geq 2,$ where $i = 1$ is the first block)

Then, the CPU 34 determines the index $R_{MAX}$ and $r_{MAX}$ in accordance with the following operational expression, to store the same in the storage areas $8l1$ and $8l2$ of the RAM 35:

$$R_{MAX} = 1/b$$

Although three time blocks are provided in the above embodiment, any number of such time blocks may be used provided at least two, are used and the accuracy is improved as the number of time blocks is increased.

Although $1/C_{g1}$, $1/C_{g2}$ and $1/C_{g3}$ are plotted along the abscissa, this is a simplified approach and the index $R_{MAX}$ can be more correctly measured by evaluating the coefficient $A_1$ on the basis of the following operational expression to assume the coefficient $A_1$ as a coefficient $C_{01}$, and similarly evaluating coefficients $C_{02}$ and $C_{03}$ to create the data as shown in FIG. 22. Assuming that $T_1 = 5$ min. and the dose of ICG is $D_1$ mg/kg, $CO_1$ may correspond to $D_1$, $D_2$ may be equal to $D_1 \times CO_2/CO_1$ and $D_3$ may be equal to $D_1 \times CO_1/CO_3$. $D_1$ may be previously set at 2 mg/kg, for example, as a value specific to the apparatus, or may be inputted by input means connected to the CPU 34.

According to the present invention as hereinabove described, vital tissue is exposed to a first light of a wavelength absorbed by specific dye dosed by injection into the blood of the vital tissue, said dye to be taken in and removed by the liver and a second light of a wavelength not absorbed by the dye and first and second photoelectric conversion signals corresponding to the first light and the second light obtained after passing through the vital tissue, are sampled so that the coefficient of a regression line expression between the first and second photoelectric conversion signals is determined on the basis of variable components in the blood included in the sampled first and second photoelectric conversion signals, thereby to produce a value correlated with a specific dye concentration in the blood on the basis of a sampling signal during a prescribed period after a lapse of a predetermined time from the injection of the specific dye and the determined coefficient of the regression line expression. Thus, the value correlated with the specific dye concentration is processed to remove factors caused by a blood flow disturbance and by any vibration of an organism for which the present tests are to be made with the aid of a sensor secured to the organism, by performing a biocalibration, thereby to more correctly test/diagnose the liver function.

Although the present invention has been described and illustrated in detail, it is clearly understood that the same is by way of illustration and example only and is not to be taken by way of limitation, the spirit and scope of the present invention being limited only by the terms of the appended claims.

INDUSTRIAL APPLICABILITY

The liver function testing apparatus according to the present invention is employed as an apparatus for testing/diagnosing the liver function by performing a biocalibration before injecting a specific dye selectively taken in and removed by the liver, into the blood for removing undersirable factors and thereafter injecting the specific dye into the blood to more correctly measure the blood plasma disappearance rate and the retention rate.

We claim:

1. An apparatus for testing the function of a liver, comprising light source means for exposing vital tissue to a first light of a wavelength absorbed by a specific dye injected as a dose into blood of said vital tissue, said specific dye to be taken in and removed by the liver, and to a second light of a wavelength not absorbed by said specific dye; photoelectric conversion means for outputting first and second photoelectric conversion signals corresponding to said first light and to said second light applied to said vital tissue by said light source means and obtained from said vital tissue as said first and second light has passed through said vital tissue; sampling means for sampling said first and second photoelectric conversion signals to provide sampling signal outputs; decision means for deciding a coefficient of a regression line expression between said first and second photoelectric conversion signals on the basis of variable components in said blood included in said first and second photoelectric conversion signals sampled by said sampling means; and arithmetic means connected to receive a value correlated to a specific dye concentration in said blood on the basis of said sampling signal output of said sampling means during a prescribed period of time from an injection of a dose of said specific dye, and connected to receive said coefficient of said regression line expression decided by said decision means for calculating a liver test result based on said sampling signal outputs and on said coefficient.

2. The liver function testing apparatus in accordance with claim 1, wherein said sampling means includes repeating sampling means for sampling said first and second photoelectric conversion signals a plurality of times, and wherein said means for deciding said coefficient of said regression line expression includes means for obtaining constants A and B by performing a regression line analysis in accordance with the following processing expression:

$$\log CL_1 = A \cdot \log CL_2 + B, \text{ wherein}$$

$CL_1$ and $CL_2$ represent average values of said first and second photoelectric conversion signals repeatedly sampled by said repeating sampling means.

3. The liver function testing apparatus in accordance with claim 2, wherein said arithmetic means includes means for data processing including data, wherein $L_1$ and $L_2$ represent values sampled from said first and second photoelectric conversion signals, a value $C_g$ correlated with said specific dye concentration on the basis of said constants A and B obtained by said obtaining means and the maximum value $L_{10}$ in accordance with the following processing expression:

$$C_g = \frac{\log L_{10}[\log L_1 - (A \cdot \log L_2 + B)]}{2\log L_{10} - (A \cdot \log L_2 + B)}.$$

4. The liver function testing apparatus in accordance with claim 1, further including coefficient calculating means for obtaining a coefficient of a simulation function as a function of time by using the method of least squares on the basis of said value correlated with said specific dye concentration processed by said arithmetic means.

5. The liver function testing apparatus in accordance with claim 4, further including means for obtaining a blood plasma disappearance rate k of said specific dye on the basis of said coefficient of said simulation function.

6. The liver function testing apparatus in accordance with claim 5, further including means for outputting said blood plasma disappearance rate obtained by said means for obtaining said blood plasma disappearance rate.

7. The liver function testing apparatus in accordance with claim 4, further including means for obtaining a retention rate R % of said specific dye in said prescribed period of time (T) on the basis of said coefficient of said simulation function.

8. The liver function testing apparatus in accordance with claim 7, further including means for outputting said retention rate.

9. The liver function testing apparatus in accordance with claim 7, wherein said means for obtaining includes means for calculating said retention rate R % based on the following expression:

$$R \% = e^{BT},$$

wherein e is the base of natural logarithms, B is a constant, and T is time.

10. The liver function testing apparatus in accordance with claim 5, wherein said means for obtaining includes means for calculating, said blood plasma disapearance rate k based on the following expression:

$$k = -B, \text{ wherein}$$

B is a constant.

11. The liver function testing apparatus in accordance with claim 4, further including means for calculating an index $R_{MAX}$ expressing a total amount of a hepatic cell function.

12. The liver function testing apparatus in accordance with claim 11, wherein said means for calculating said index $R_{MAX}$ includes means for injecting said specific dye, and computer means for dividing a prescribed time interval from a uniform distribution of said specific dye in said blood, into a plurality of blocks to obtain coefficients $A_i$ and $B_i$ on the basis of simulation functions $C_g = A_i e^{B_i t}$, wherein $i = 1, 2, \ldots, m, m \geq 2$, wherein $i = 1$ is a first block, in respective ones of said blocks, computer means for calculating values of $C_g$ at initial times of respective ones of said blocks as $C_i$ based on the assumption that coefficients $K_i = -B_i$, and computer means for performing a regression line analysis on the basis of said coefficients $K_i$ and values of $C_i$ based on an expression of $(1/K_i)=a(1/C_i)+b$ to obtain coefficients a and b and to determine said index as $R_{MAX}=1/b$.

13. The liver function testing apparatus in accordance with claim 11, wherein said means for obtaining said index $R_{MAX}$ includes means for injecting said specific dye, computer means for dividing a prescribed time interval from a uniform distribution of said specific dye in said blood into a plurality of blocks to obtain coefficients $A_i$ and $B_i$ on the basis of simulation functions of $Cg=A_i e^{B_i t}$, wherein $i=1, 2, \ldots, m$, $m\geq 2$, where $i=1$ is a first block, in respective ones of said blocks, computer means for calculating a load quantity $D_i$ on the basis of said coefficients $A_i$ and on the basis of a load quantity $D_1$ of said specific dye, whereby $D_i$ is defined by the expression $D_i=D_1\times A_i/A_1$ and $K_i=-B_i$, and computer means for performing a regression line analysis based on the following expression of $(1/K_i)=C(1/D_i)+d$ wherein $K_i$ and $D_i$ are defined as set forth above to obtain coefficients C and d, thereby to obtain said index $R_{MAX}$ from $R_{MAX}=1/d$.

14. The liver function testing apparatus in accordance with claim 4, wherein said coefficient calculating means includes means for determining said constants A and B on the basis of the following operation expression:

$Cg=Ae^{Bt}$, wherein t represents said prescribed period of time after injection of said specific dye.

15. The liver function testing apparatus in accordance with claim 4, wherein
said coefficient calculating means includes means for determining correlation coefficient of said simulation function.

16. The liver function testing apparatus in accordance with claim 15, further including informing means for giving an alarm when said correlation coefficient of said simulation function is greater than a predetermined value.

17. The liver function testing apparatus in accordance with claim 1, wherein
said decision means includes computer means for calculating a correlation coefficient of said regression line expression.

18. The liver function testing apparatus in accordance with claim 17, further including informing means for giving an alarm when said correlation coefficient is greater than a predetermined value.

19. The liver function testing apparatus in accordance with claim 1, further including mode selection means for selecting a biocalibration mode for deciding said coefficient of said regression line expression by said decision means, and a measurement mode for for measuring said value correlated with said specific dye concentration by said arithmertic means.

20. The liver function testing apparatus in accordance with claim 19, further including means for activating said decision means in response to a selection of said biocalibration mode by said mode selection means.

21. The liver function testing apparatus in accordance with claim 19, further including means for activating said arithmetic means in response to a selection of said measurement mode by said mode selection means.

22. The liver function testing apparatus in accordance with claim 1, further including means for setting intensity levels of said first light and of said second light emitted by said light source means so that respective levels of said first and second photoelectric conversion signals are within a predetermined range.

23. A method for testing the function of a liver, comprising the steps of exposing vital tissue to a first light of a wavelength absorbed by a specific dye injected into blood of said vital tissue said specific dye to be taken in and removed by the liver, and to a second light of a wavelength not absorbed by said dye; sampling photoelectric conversion signals corresponding to said first light and to said second light applied to said vital tissue and obtained from said vital tissue in a biocalibration mode as said first and second light has passed through said vital tissue; deciding a coefficient of a regression line expression between said first and second photoelectric conversion signals on the basis of variable components in said blood included in respective sampling outputs obtained in said biocalibration mode; injecting said specific dye into said blood and thereafter sampling said first and second photoelectric conversion signals during a prescribed period of time in a measurement mode; and calculating a value correlated with a specific dye concentration in said blood on the basis of respective sampling outputs and on the basis of said coefficient of said regression line expression in said measurement mode for providing a calculated liver test result based on said sampling outputs and on said coefficient.

24. The liver function testing method in accordance with claim 23, further including the step of obtaining a coefficient of a simulation function as a function of time by using the method of least squares on the basis of said value correlated with said specific dye concentration.

25. The liver function testing method in accordance with claim 24, further including the step of calculating a blood plasma disappearance rate of said specific dye on the basis of said coefficient of said simulation function.

26. The liver function testing method in accordance with claim 24, further including the step of calculating a retention rate of said specific dye in said prescribed period of time on the basis of said coefficient of said simulation function.

27. The liver function testing method in accordance with claim 24, further including the step of calculating an index expressing the total amount of hepatic cell function on the basis of said obtained coefficient of said simulation function.

28. The liver function testing method in accordance with claim 27, wherein said step of calculating said index expressing said total amount of hepatic cell function includes the step of injecting said specific dye, dividing a prescribed time interval starting from a uniform distribution of said specific dye in said blood, into a plurality of blocks to obtain coefficients $A_i$ and $B_i$ on the basis of said simulation functions of $Cg=A_i e^{B_i t}$, wherein, $i=1, 2, \ldots, m$, $m\geq 2$, where $i=1$ is a first block, in respective ones of said blocks for determining values of Cg at initial times in respective ones of said blocks as $C_i$ assuming that $k_i=-B_i$, and performing a regression line analysis on the basis of said coefficients $K_i$ and $C_i$ by using an expression of $(1/K_i)=a(1/C_i+b$ to obtain coefficients a and b for expressing said total amount of said hepatic cell function as $R_{MAX}=1/b$.

29. The liver function testing method in accordance with claim 27, wherein said step of calculating said index expressing said total amount of said hepatic cell function includes the step of injecting said specific dye, dividing a prescribed time interval starting from a uniform distribution of said specific dye in said blood, into a plurality of blocks to obtain coefficients $A_i$ and $B_i$ on the basis of said simulation functions of $Cg = A_i e^{B_i t}$, wherein $i = 1, 2, \ldots, m$, $m \geq 2$, where $i = 1$ is a first block, in respective ones of said blocks and for determining, on the basis of said coefficients $A_i$ and a load quantity $D_1$ of said specific dye, $D_i$ from an expression of $D_i = D_1 \cdot A_i / A_1$ assuming that $K_i = -B_i$, and performing a regression line analysis on the basis of $K_i$ and $D_i$ by using an operation expression of $(1/K_i) = C(1/D_i)$ to obtain coefficients C and d, thereby to obtain said index $R_{MAX}$.

30. The liver function testing method in accordance with claim 23, wherein said sampling includes the step of sampling said first and second photoelectric conversion signals a plurality of times, performing a regression line analysis for obtaining constants A and B based on an assumption that $CL_1$ and $CL_2$ represent average values of said first and second photoelectric conversion signals sampled said plurality of times, and in accordance with the following regression line expression:

$$\log CL_1 = A \cdot \log CL_2 + B, \text{ and}$$

assuming for said deciding of said coefficient of said regression line expression that $L_{10}$ represents the maximum sampled value of said first photoelectric conversion signal.

31. The liver function testing method in accordance with claim 30, further including the step of calculating, a value Cg correlated with said specific dye concentration based on the following expression:

$$Cg = \frac{\log L_{10}[\log L_1 - (A \cdot \log L_2 + B)]}{2\log L_{10} - (A \cdot \log L_2 + B)},$$

wherein A and B are constants, $L_{10}$ is the maximum value, and $L_1$ and $L_2$ represent sampled values of said first and second photoelectric conversion signals.

32. A liver function testing apparatus for testing liver function, comprising light source means for exposing vital tissue to a first light of a wavelength absorbed by a specific dye injected as a dose into blood of said vital tissue, said dye to be taken in and removed by the liver and second light of a wavelength not absorbed by said specific dye; photoelectric conversion means for outputting first and second photoelectric conversion signals corresponding to said first light and said second light applied to said vital tissue by said light source means and obtained from said vital tissue; sampling means for sampling said first and second photoelectric conversion signals during a prescribed period after a lapse of a predetermined time from an injection of said specific dye; arithmetic means for calculating a correlation coefficient correlated with a specific dye concentration in said blood on the basis of sampling values sampled by said sampling means; and informing means for giving an alarm when said correlation coefficient correlated with a specific dye concentration is greater than a predetermined value.

* * * * *

UNITED STATES PATENT AND TRADEMARK OFFICE
CERTIFICATE OF CORRECTION

PATENT NO. : 4,905,703

DATED : March 6, 1990

INVENTOR(S) : Masahiko Kanda et al.

It is certified that error appears in the above-identified patent and that said Letters Patent is hereby corrected as shown below:

In the Abstract [57], line 3, before "blood" insert --the--;

line 5, replace "a liver" by --the liver,-- line 18, before "which" insert --,--;

line 19, after "time" insert --,--;

Claim 10, Column 14, line 47, replace "disapearance" by --disappearance--;

Claim 13, Column 15, line 12, replace "m = 2" by

--m $\geq$ 2--;

Claim 15, Column 15, line 33, after

"determining" insert --a--;

Claim 19, Column 15, line 53 delete "for"; (second occurrence);

Claim 27 Column 16, line 45 delete --obtained--;

Claim 28, Column 16, line 60 replace "=a(1/$C_i$ + b" by-- =a(1/$C_i$) + b--;

UNITED STATES PATENT AND TRADEMARK OFFICE
CERTIFICATE OF CORRECTION

PATENT NO. : 4,905,703

DATED : March 6, 1990

INVENTOR(S) : Masahiko Kanda et al.

It is certified that error appears in the above-identified patent and that said Letters Patent is hereby corrected as shown below:

Claim 29, Column 17, line 8 replace "$D_i = D_1 \cdot A_i / A_1$" by --$D_i = D_1 \cdot A_i / A_1$--;

Claim 30, Column 17, line 22 replace "$\log CL_1 = A \cdot \log CL_2 + B$" by --$\log CL_1 = A \cdot \log CL_2 + B$--.

Signed and Sealed this

Fourteenth Day of January, 1992

Attest:

HARRY F. MANBECK, JR.

Attesting Officer

Commissioner of Patents and Trademarks